US012623085B2

(12) United States Patent (10) Patent No.: US 12,623,085 B2

Possover (45) Date of Patent: \*May 12, 2026

(54) IMPLANTABLE NEURO MODULATOR DEVICE AND SYSTEM COMPRISING SUCH AN IMPLANTABLE NEURO MODULATOR DEVICE

(71) Applicant: NeuroGyn AG, Baar (CH)

(72) Inventor: Marc Possover, Hagendorn (CH)

(73) Assignee: NeuroGyn AG, Baar (CH)

( \* ) Notice: Subject to any disclaimer, the term of this patent is extended or adjusted under 35 U.S.C. 154(b) by 0 days.

This patent is subject to a terminal disclaimer.

(21) Appl. No.: 19/176,550

(22) Filed: Apr. 11, 2025

(65) Prior Publication Data

US 2025/0242160 A1 Jul. 31, 2025

Related U.S. Application Data

(63) Continuation of application No. PCT/EP2022/078276, filed on Oct. 11, 2022.

(51) Int. Cl.
| | |
|---|---|
| *A61N 1/375* | (2006.01) |
| *A61N 1/05* | (2006.01) |
| *A61N 1/36* | (2006.01) |
| *A61N 1/378* | (2006.01) |
| *G16H 40/67* | (2018.01) |

(52) U.S. Cl.
CPC ......... *A61N 1/3754* (2013.01); *A61N 1/0551* (2013.01); *A61N 1/36125* (2013.01); *A61N 1/36171* (2013.01); *A61N 1/36175* (2013.01);

*A61N 1/37518* (2017.08); *A61N 1/3758* (2013.01); *A61N 1/3787* (2013.01); *G16H 40/67* (2018.01)

(58) Field of Classification Search
CPC ............ A61N 1/36007; A61N 1/36125; A61N 1/3605; A61N 1/36171; A61N 1/36175; A61N 1/37229; A61N 1/375; A61N 1/37518; A61N 1/3754; A61N 1/3758; A61N 1/3787; A61N 1/0551
See application file for complete search history.

(56) References Cited

U.S. PATENT DOCUMENTS

| | | | |
|---|---|---|---|
| 2006/0079936 A1* | 4/2006 | Boveja | ............... A61N 1/36082 |
| | | | 607/2 |
| 2011/0288615 A1* | 11/2011 | Armstrong | ........... A61B 5/0031 |
| | | | 607/2 |
| 2018/0133487 A1 | 5/2018 | Shah et al. | |
| 2020/0001095 A1 | 1/2020 | Iyer et al. | |
| 2020/0101291 A1 | 4/2020 | Yakovlev et al. | |
| 2021/0154484 A1 | 5/2021 | Thom et al. | |

OTHER PUBLICATIONS

International Search Report and Written Opinion dated May 15, 2023, issued in corresponding application PCT/EP2022/078276.

\* cited by examiner

*Primary Examiner* — George Manuel

(74) *Attorney, Agent, or Firm* — Bachman & LaPointe, P.C.

(57) ABSTRACT

An implantable neuro-modulator device, including a hermetically sealed housing, wherein an antenna for communicating with external devices and/or for wirelessly receiving electrical energy is positioned within the housing, wherein a major part of the housing is electromagnetically transparent to radiation in the frequency range below 20 MHz, in particular between 5 and 15 MHz.

20 Claims, 5 Drawing Sheets

IMPLANTABLE NEURO MODULATOR DEVICE AND SYSTEM COMPRISING SUCH AN IMPLANTABLE NEURO MODULATOR DEVICE

BACKGROUND OF THE INVENTION

The current invention relates to an implantable neuro modulator device and a system comprising an implantable neuro modulator device.

It is already known from the prior art to use implantable devices for stimulating muscles for externally triggered muscle contraction, especially in pacemaker devices, such as a cardiac pacemakers or other pacemakers. For those applications an implantable device comprising an energy storage device, and respective electronics for energy management and also for creating and outputting electric trigger impulses to an output port which in turn is connected to an electrode lead are known. The state of the art already teaches pacemaker devices which can be recharged with electrical energy wirelessly. Also the transmission of control data, especially control parameters via a wireless connection, is known from the prior art of pacemakers.

The field of neuro modulator devices comprises different types of implantable devices. The implantable neuro modulator devices are used to provide stimulus to nerves, especially via electric pulses, for example in the pelvic region. Accordingly, the implantable neuro modulator devices do not directly cause a physical response by the patient body, such as the contraction of a muscle. However, in the rather young medical field of neuro modulation, it has been found that a lot of pathologic physical conditions of the body of a patient can be relieved or even cured based on the modulation of nerves by implantable new modulator devices. Those conditions include but are not limited to the treatment of erectile dysfunction, fecal incontinence, decubitus and paraplegics. There are further very strong indicators that also psychological indications, such as depression, can be treated and/or cured by neuro modulation of nerves.

Even though a muscle stimulation by a pacemaker and the modulation of a nerve are based on the same principle of an electric impulse provided by a preferably implanted device, the different applications as well as technical and medical requirements resulting from those applications differ significantly between the field of muscle stimulation and nerve modulation.

Previously, the implantation of neuro modulator devices was generally limited by two basic restrictions. First of all, the surgical methods and procedures to implant a neuro modulator device into a body were rather complicated and required very high skills of the respective surgeon. Additionally, the neuro modulator devices known from the prior art rather uncomfortable to the user, especially due to their size. When implanted into certain parts of the body of a user an implant can be felt or recognized by a user during body movement or even without movement when the implant exceeds a certain volume or size. This is at east uncomfortable to the user/patient bur may also cause pain and/or inflection.

SUMMARY OF THE INVENTION

Based on this prior art it is the objective of the current invention to suggest an implantable neuro modulator device and a system comprising such an implantable neuro modulator device which allow easy implantation or which are especially adopted to simple implantation procedures and which is more comfortable for the user after implantation.

These problems are solved by an implantable neuro modulator device as well as a neuro modulator system as disclosed herein. Preferred embodiments of the claimed invention are provided by the dependent claims, the following description especially the drawings, the description of the drawings and the general description.

All aspects or features which are hereinafter disclosed or described as device features shall also be considered to be disclosed as part of respective methods and shall also be claimable as methods, and vice versa.

The implantable neuro modulator device according to the current invention comprises a hermetically sealed housing wherein an antenna for communicating with external devices and/or for wirelessly receiving electrical energy is positioned within the housing, wherein a major part of the housing is electromagnetically transparent to radiation in the frequency range below 20 MHz, in particular between 5 and 15 MHz.

To lower the amount of surgical procedures for a longtime or long-term use of implantable neuro modulator devices it is important to be able to recharge the electrical energy storage device wirelessly and/or to be able to adapt the use of the neuro modulator device to the patient's needs wirelessly, i.e. without additional surgical procedures.

Although devices are known, which enable electromagnetic communication and/or electromagnetic energy transfer, those devices previously had the housing made up of generally at least two major parts, one of which was electromagnetically transparent and the other one was electromagnetically opaque. This known setup comes with two major drawbacks. First of all, the housing becomes rather bulky and space consuming. Secondly, the known set-ups only enable or provide for a rather small antenna, i.e. an antenna with a relatively small receiving cross section. Thus, the relative alignment between the implant and the antenna on one hand and the devices or parts of the infrastructure which are used for electromagnetic communication and/or electromagnetic energy transfer has to be very precise. This is a challenge since every living body shows constant internal movements which may impact the position of the implant on a small scale. Also the body exterior device which us used for communication and/or energy transfer needs to be positioned very precise and static, which is again very demanding when a living and moving body of a user is positioned in very close proximity. The first drawback of a large or space consuming housing also had a direct impact onto the surgical procedures to implant the known devices. The larger the implantable device, the more complicated the surgical procedure becomes to implant and secure the implanted neuro modulator device in the body. Additionally, the patient's quality of living is also more adversely affected the bigger the implanted device is.

It has been surprisingly realized by the current invention that a housing that is almost entirely made of material that is electromagnetically transparent to radiation in the frequency range below 20 MHz enables a very compact setup of the implantable neuro modulator device, without compromising other important aspects of the device such as biocompatibility, stability or the like. This allows easier implantation procedures and also drastically reduces the amount of resources, especially implantable, and therefore, biocompatible material or resources, which makes the implantable neuro modulator according to the present invention not only a lot smaller, especially much less space consuming, but also enables the use of a much larger antenna, especially an antenna with a much larger receiving cross section.

A preferred embodiment of the invention requires the housing to be made of at least 70% of its surface to be electromagnetically transparent. The materials, which are among others considered to be electromagnetically transparent in the said frequency range, are ceramic materials, plastic material, glass, resin or combinations thereof. Those materials which are known for biocompatibility in the field of implants are preferred materials that can exhibit the required transparency for electromagnetic radiation below 20 MHz.

According to a preferred embodiment, the housing has a round cross section, preferably with a tubular or cylindrical shape, and comprises a first and a second housing part, wherein the first housing part comprises a container with a round cross section which is closed and preferably rounded at one end and has a first sealing ring at the opposite or second end. The round cross section of the housing reduces the length of incisions required during the surgical implantation of the device, especially if the device can be implanted essentially by movement along a longitudinal axis that runs basically perpendicular to the round cross section. The preferred rounded end of the first housing part enables an easy introduction into and advancement in the body during the implantation. The preferred sealing ring enables and facilitates connection between the first housing part and the second housing part to form a hermetically sealed housing.

The container of the first housing part is preferably shaped in such a way and comprises such dimensions, that in the sealed state of the housing the container and/or the first housing part will take up or enclose the most of the internal parts and components of the neuro modulator device. Thus, the first housing part may provide for the majority of the volume of neuro modulator device whereas the second housing part has more of a shape and function as a lid or cap.

In a further preferred embodiment, the container, preferably together with the closed, preferably rounded, end, is/are machined, especially turned, from a monolithic piece of material, especially ceramics material. This allows the greatest part of the housing, concerning surface and enclosed volume, to be provided by a single and monolithic piece of material without the need of joints and/or sealings. Although such a monolithic piece of ceramic material is not easy to provide, it has been surprisingly proven, that the advantages reached through the electromagnetic transparency and the absence of joints and connections or sealings, which are possible sources of damage to the hermetical sealing of the housing outdraw the requirements to provide such a monolithic piece of ceramic material.

The machining of the container may be limited to certain parts or regions of the volume or surface of the container. Especially the surfaces that are critical for a hermetical sealing of the housing can be machined to achieve the necessary precision. For other parts of the container, the machining may not be necessary as the needed precision may be lower and/or the respective surface forms can also be achieved by other forming methods and procedures, such as molding, extruding, additive manufacturing or the like.

According to a further preferred embodiment, the second housing part comprises a second sealing ring and a feed-through element, the feed-through element comprising at least one opening in which an electrical contact element may electrically connect one side of the feed-through element with a second side of the feed-through element.

The second sealing ring is preferably provided with the same cross section, especially the same exterior cross section as the first sealing ring, such that when the first sealing ring and the second sealing ring are joined to provide the hermetically sealed housing, there is, especially apart from the sealing itself, a flush or continuous outer surface over the first and second sealing ring.

The feed-through element is preferably provided as a further monolithic piece of material, especially ceramics material, which not only adds to the electromagnetically transparent surface of the housing but also serves as a good electrical isolator for DC- and AC-currents, which is essential for such a feed-through element. Accordingly, the feed-through element may also comprise or may be made of different isolator-materials, such as glass, resin, plastics or the like. The feed-through element preferably has a disk shape or a sphere, a ball shape or a lentil or lens shape. In a preferred embodiment the feed-through element can be entirely arranged in an inner opening of the second sealing ring such that in a longitudinal direction the second sealing ring or one distal end of the second sealing ring forms one end of the housing.

According to a further preferred embodiment, the feed-through element may comprise at least four openings preferably arranged at two different height levels, the height levels being defined by lines perpendicular to a diameter line through the center of the feed-through element.

The embodiment with at least four openings in the feed-through element allows for the respective connections to an electrode lead with at least four electrodes. With the openings arranged at different height levels, it is possible to contact the electrical contact elements running through the openings on different sides of the support member or carrier, such as a PCB (Printed Circuit Board) on different sides or on different surfaces of carrier, thereby allowing very densely packed arrangement of the electrical contact elements.

A further preferred embodiment requires that the two openings with a smaller distance between them along the height level are placed on a height level closer to the center of the feed-through element than the openings with the greater distance between them along a height level.

In another preferred embodiment, the contact element is electrically connected to an electrode lead, for outputting modulation pulses to a patient. The connection between the contact element, which may be realized as a copper pin, and the electrode lead may be achieved by a solder connection. Thus, the connection may be established as an primarily electrical connection. However, the connection, such as a solder connection may also add substantially to the mechanical connection of the parts, thereby providing as substantial mechanical strength.

In any case the electric contact elements passing through the feed-through element are electrically isolated from each other for both, AC- and DC-currents.

In a further preferred embodiment, the electrode lead of the device is mechanically connected to the device in a permanent or non-detachable manner. This preferably includes the electrode lead up to the point from which electrical pulses are outputted to body/patient. In other words the device also comprises an non-detachably connected complete electrode lead. The mechanical connection may be realized together with the electrical connection, i.e. with the contact element. However, it may be advantageous, if the mechanical connection between the housing and the electrode lead is alternatively or additionally strengthened by further mechanical connections, as will be discussed in more detail below. It was surprisingly found that even with a non-detachably connected electrode lead, the inventive neuro modulator device can easily implanted into the patient's or user's body.

In a further preferred embodiment, the first and/or second sealing ring is/are made of metallic material, especially titanium and/or surgical steel. These materials are well established in the field of implants and further allows reliable high quality connections or sealings between the first and second sealing ring, preferably by gold brazing connections.

According to a further preferred embodiment, the first and second housing parts are sealed with each other by a sealing, preferably gold brazing, connecting the first and second sealing ring. In a further preferred embodiment only three types of sealings or connections have to be established to form the hermetically sealed housing or to hermetically seal the housing. The first type of connection is the connection or sealing between the sealing ring and the container for the first housing part and the sealing between the feed-through element and the sealing ring for the second housing part. The second type of sealing is the sealing of the openings of the feed-through element remaining outside or radially outward to the electrical contact elements. The third type of sealing or connection is the connection between the first sealing ring and the second sealing ring.

The first and the last type of connection may require to seal a ceramic material with a metallic material which can be achieved by gold brazing. The second type of connection or sealing, that is the connection between the sealing rings, can also be achieved by gold brazing. Accordingly, the entire sealing process of the housing can be achieved by forming gold brazings between the respective parts to hermetically seal the housing. This reduces the methods used in production of the device and the materials used and introduced into the patient's body.

In alternative advantageous embodiments, other types of connections may also be used. Alternatively, some connections may not be necessary at all, For example, if the feed-through element is made of a molded resin or plastic element which is molded into the second sealing ring and into which the contact elements are embedded. In this and similar embodiment there is no need for an extra connection between the respective parts.

In a further, preferred embodiment the neuro modulator device comprises an overmold including molded header, preferably made of biocompatible polymeric resin, the molded header covering at least parts of the electrical contact element and the respective openings in the feed-through element on one side of the feed-through element, especially at the exterior side of the feed-through element.

The molded header can be used to allow for secure connection or secure transmission between the housing of the neuro modulator on one side and the electrode lead on the other side. It may also be part of the connection between the device and its permanently connected electrode lead. It may be further used to improve the hermetic sealing of the housing by further protecting the space in-between the openings in the feed-through element and the electrical contact elements.

According to a preferred embodiment the overmold may comprise at least one opening and/or at least one suture hole for autologous fixation of the device and/or suturing the device to tissue material or bone material. The molded header is one preferred place to realize a suture hole, because the suture hole can be formed, especially molded together with the molded header, without the risk that the hermetical sealing of the housing could be endangered by the suture hole. Other advantageous placements of the opening(s) or suture holes are possible.

In a further preferred embodiment, the neuro modulator device may comprise an overmold, preferably made of biocompatible polymeric resin, covering the entire first and second housing part and preferably forming a molded header and/or a fixation wing. In those embodiments the overmold covering the entire housing enables that only one single material of the neuro modulator device will come into contact with the interior of the body in which the device is implanted. Additionally, the overmold enables compensating manufacturing tolerances of the housing which are present to a certain degree in every manufacturing process or assembly process, thereby enabling a highly reproducible and constant final exterior of the neuro modulator device. The overmold can provide for a molded header as well as for a fixation wing, which will be described in more detail below.

The overmold can not only reduce the amount of materials which get into contact with the body into which the device is implanted but can also realize several functions such as the molded header, the suture hole by one process in the manufacturing or assembly process by a single molding process, such as an injection molding process.

A further preferred embodiment requires that the fixation wing is formed at an end of the housing, preferably adjacent to the first housing part and/or at the opposite end of the overmold which forms the molded header. Although the fixation wing at one end adjacent to the housing parts increases the overall length of the neuro modulator device, it can be preferred over a suturing hole realized within or by the molded header, since the suturing mesh wing allows a more flexible suturing by the surgeon compared to a suturing hole included in the molded header.

The fixation wing may have a structured surface on two opposite surfaces. The structure may include openings/holes connecting the two surfaces with each other. The structure may have a regular and/or recurring pattern. The structure may allow growth of tissue through or into it and may assist the autologous fixation of the device. The holes or openings may form a mesh and may be used as suture holes. Alternatively, the suture material may punch through the material of the structured surfaces of the fixation wing forming suture holes only when suturing the device to the tissue or bone.

According to a further preferred embodiment the fixation wing is formed in a plane parallel to the longitudinal axis of the housing. In a further preferred embodiment the fixation wing is formed in a central or centric plane of the round cross section of the housing. This minimizes the resistance or drag of the device during surgical insertion, especially if the devices is implanted or moved along it's longitudinal axis.

The round cross section of the device has several advantages. However, it also comes with the risk of unwanted movement of the device after implantation. The movement can be a translation along the longitudinal axis of the device and/or rotation around the longitudinal axis. The possible movements and effectively preventing those movements is critical, since the absolute and relative position of the device has a significant impact on the efficiency of data and energy transmission from outside of the body. Accordingly, the advantageous fixation wing has proven to be very effective in eliminating those movements after implantation.

In further preferred embodiments the orientation of the fixation wing and/or the guiding member/electrode lead is aligned and/or in a fixed position/orientation with other components of the device, such as the electrode lead and/or an antenna. This is very helpful for the surgeon and allows a very effective implantation of the implantable neuro modulator device. The surgeon can monitor the location and/or orientation of the fixation wing and/or the electrode lead and/or a guiding member (see below) during implantation, especially by imaging procedures such as endoscopy, ultrasonic imaging or the like. This also includes the fixation of the device to the body (tissue or bone) by suturing, especially using the fixation wing as a suturing wing. Thereby, the absolute position of the device in the body and the orientation is controlled allowing the controlled orientation of interior parts of the device also.

As discussed in more detail below, it is particularly advantageous, if the exterior of the device, such as the fixation wing, the electrode lead, the guiding member or the like have a special, preferably parallel, arrangement with respect to the interior parts of the device, especially the antenna and its receiving cross section. Since the interior of the device is not visible it is very helpful to be able to position and orientate the interior structure of the device into a wanted or advantageous position by means of positioning and orientating the exterior of the device.

A further preferred embodiment comprises an end portion of the overmold and/or molded header, opposite to the housing or the second housing part, comprising a guide member for guiding an electrode lead wherein the guide member is formed at an angle, preferably at 30° to 70°, with respect to the longitudinal axis of the housing. The angled guide member allows the electrode lead to be guided in a direction angled to the longitudinal axis of the housing which makes it easier for the electrode lead to be positioned within the body during implantation procedures. The guide member may also adapt the orientation of the electrode lead to the anatomy of the body in which the device is implanted based on the location and/or orientation in which the device is positioned and/or fixed to the body.

In a further preferred embodiment, the guide member is formed in such a way that the electrode lead is guided in a plane parallel or identical to the plane of the fixation wing. After the electrode lead exits the guide member it is of course flexible in its orientation, only limited by the flexibility of the electrode lead itself. However, within the guide member the electrode lead is guided, parallel to the fixation wing, which allows that the general of basic orientation of the electrode lead leading away from the housing and/or overmold is determined by controlling and fixing the position and/or orientation of the fixation wing. The guide member can be monolithically formed together with the rest of the molded header and/or the overmold.

In a further preferred embodiment, the diameter to length ratio of the housing's maximum diameter to the length of the housing, preferably including the molded header and/or the overmold is less than 0.35. Such a rather lengthy implantable neuro modulator device, especially when combined with a round cross section, enables surgical procedures with very small incisions and an easy implantation into the body and navigation within the body of the patient.

In a preferred embodiment, the housing has a maximum diameter of less than 12 mm, preferably less than 10 mm. In a further preferred embodiment the overmold has a maximum diameter of less than 13 mm, preferably less than 12 mm. Such small diameters need only very small incisions for the implantation procedure. Moreover, such small diameters enable placing the neuro modulator device into the body in such a fashion that it cannot be felt or recognized by the patient after the implantation.

According to a further embodiment of the invention the length of the housing, preferably including the molded header and/or the overmold, is less than 50 mm, preferably less than 46 mm, especially less than 44 mm. This relatively small length of the neuro modulator device, especially in combination with small maximum diameters, result in a very small and compact neuro modulator device, can further be implanted with relatively easy surgical procedures and can further be placed into the body or can be implanted into a body without the patient feeling or recognizing the implant, especially during all sorts of physical activities, after the implantation.

In a further preferred embodiment of the invention, additionally to at least one antenna, one rechargeable energy storing device, one electrical control unit and a pulse generating means are arranged within the housing. In an especially preferred embodiment, the implantable neuro-modulator device only comprises a single antenna that is used for data/information transmission (sending/receiving) as well as energy reception or charging of the rechargeable energy storage device.

This allows for long term use of the neuro modulator device and initial implantation without the need of further surgical procedures allowing to recharge the device and further enabling to adapt the control parameters of the device externally after implantation.

In a preferred embodiment the rechargeable energy storage device is a solid state battery, preferably two solid state batteries. This sort of energy storage devices have several advantages over other energy storage devices such as lithium ion batteries/accumulators, especially with respect to long term use or high numbers of charging or recharging cycles.

The use of two solid state batteries has the advantages that the device may still be operated safely and my output stimulation pulses, even if one battery is inactive, for example due to charging activities or due to malfunctioning or damage.

A further preferred embodiment of the invention requires the electrical control unit to comprise two charging circuits each of one being set up for charging an individual rechargeable energy storage device. As mentioned above, those independent charging circuits enable to charge the device or the energy storing devices while performing nerve modulation by outputting electrical impulses to an electrode lead or an electrode.

This enables minimizing the total number of charging cycles per energy storage device, thereby maximizing the lifetime of the respective energy storage device.

According to a further preferred embodiment the neuro modulator device comprises a rigid support member, preferably made of fiber reinforced resin, especially a printed circuit board, within the housing. This support member can be used to mechanically support and electrically connect most of the electronics or electrical components of the neuro modulator device, such as micro controllers, pulse generating means and electrical control components.

In a further preferred embodiment the support member extends essentially over the entire length and the entire width of an internal space confined by the housing, preferably at a certain eccentric height level of the housing, dividing the space confined by the housing into a first, smaller and second, lager cavity of the housing, each of one defined by parts of the housing and one side of the support member, respectively.

In one particularly preferred embodiment, at least one rechargeable energy storage device, preferably all rechargeable energy storage devices, is/are placed in the second, larger cavity of the housing.

In another preferred embodiment the openings in the feed-through element, especially the height levels and/or the electrical contact elements, are arranged in such a fashion that two of the electrical contact elements are arranged in the second cavity at an inner side of the feed-through element and two electrical contact elements are arranged in the first cavity of the housing at an inner side of the feed-through element.

According to another preferred embodiment of the invention, the at least one antenna, preferably the only antenna, is designed as a large aperture antenna, preferably with a receiving cross section of more than 0.1*A*B, preferably 0.2*A*B, especially 0.4*A*B, A being the length of the housing and B being the width or diameter of the housing. A large aperture antenna enables a sufficiently efficient energy transmission within a comparatively small housing and also a large tolerance for the relative placement or arrangement of another antenna for coupling with the antenna of the device. For this setup it is necessary that the antenna is orientated or arranged relatively close to the inner surfaces of the housing parts to reach a maximum aperture possible within the housing. The large aperture antenna makes it possible to have an efficient energy transmission and control communication whilst keeping the entire volume of the neuro modulator device at a minimum.

In a further preferred embodiment the receiving cross section of the antenna is aligned parallel to a fixation wing of the overmold and/or parallel to the guide member of the molded header.

In a further preferred embodiment the at least one antenna, preferably only any antenna, is designed with a thickness at right angle to the receiving cross section of less than 3 mm, preferably less than 2 mm. Thereby it is possible to fit the antenna into the interior of the rounded cross section of the housing.

In a further preferred embodiment, the at least one antenna, preferably only antenna, comprises a coil, preferably of an essentially rectangular shape, wherein the coil is arranged at an angle, preferably at a right angle, to the plane of the support member. This arrangement of the antenna with respect to the support member makes it possible to very densely pack all the interior components into the housing without negatively effecting the possible aperture of the antenna or the aperture surface of the antenna within the housing.

In a preferred embodiment, the antenna coil is arranged in the first and second cavity of the housing and the coil passes through passageways in the support member, the passageways being arranged at two opposite ends of the support members, preferably in a length or longitudinal direction. This embodiment also allows for the antenna to have a maximized aperture or receiving cross section with the space confined by the housing.

According to a further preferred embodiment, the antenna comprises a printed circuit board with several different layers, each of the layers of the board carrying at these one winding of the antenna coil being arranged parallel and adjacent to one another. This provides the necessary coil length by a convenient stacking of circuit board layers. The coil or coil parts of the antenna can be printed onto the circuit boards.

In a further preferred embodiment, the support member comprises cutouts at at least one end in a length/longitudinal direction of the support member, allowing to position, preferably slide, the antenna into the passageways. The cutouts provide for an easy way to assemble the neuro modulator device.

For example, the support member, possibly also carrying the energy storage device or devices on one side thereof and other electrical components on one or both sides thereof can be preassembled. In a next assembly step the preassembled antenna can be placed, especially slided over the support member, facilitated by the cutout and arriving in the passageways so that the antenna passes the support member on both ends of the support member at an angle, preferably at a right angle with respect to the plane of the support member. Then, the assembly of the support member with the electrical or electronic components, possibly already including energy storage devices and the antenna, possibly after connecting the antenna to the support member electrically and/or mechanically, can be put into the first housing part. After that the second housing part can be put on top of the first housing part such that the sealing rings get into contact with each other. In this step the electronic contact elements, which can be preassembled or connected to the support member in advance can be fed through the openings in the feed-through element. After that the housing can be sealed, especially by sealing the two sealing rings with a gold brazing and by sealing the space between the openings and the feed-through elements and the electrical contact elements. The connection or sealing between the container and the first sealing ring as well as between the second sealing ring and the feed-through element can be realized or can be formed prior to connecting the first housing part and the second housing part. After this the electrical contact elements can be connected to the electrode or electrode lead before the molded header or overmold is molded over parts of the housing or the entire housing.

In another preferred embodiment, the neuro modulator device may include a sensor to measure the temperature in the vicinity of the implant. This allows to identify inflammation reactions of the body or fever of the patient. The modulator device may further include means to transmit the measured temperature via the at least one antenna, preferably via the only antenna.

The above identified technical problem is also solved by a system comprising an neuro modulator device according to any of the previous embodiments and wearable and/or handheld electronic device wherein the wearable and/or handheld electronic device comprises an energy storage device and a communication interface for establishing a communication connection with the neuro modulator device.

The wearable and/or handheld device (hereinafter called: wearable electronic device) may be designed as a patient or user device for regular use of a patient or user. It is preferred that the energy storage device of the wearable device can be recharged, for example via a galvanic cable connection, preferably using a cradle device with charging contactor a detachable cable or via wireless energy transfer or transmission. The communication interface can rely on standard communication protocols such as NFC, BLE, RFID or the like. However, other communication protocols may be used by the communication interface. The system comprising the neuro modulator and the wearable device enables the patient to conveniently use the neuro modulator device over a long period of time since it provides the infrastructure or necessary means to communicate with the implanted neuro modulator device and to recharge the implanted neuro modulator device.

According to a preferred embodiment, the wearable electronic device comprises a wireless energy transmitting unit connected with the energy storage device of the wearable device, the energy transmitting unit being adopted to transmit energy to the neuro modulator device and the neuro modulator device being adapted to receive the transmitted energy and to store it, preferably receiving the transmitted energy by the at least one, preferably only, antenna of the neuro modulator device and storing the received energy in the rechargeable storage device of the modulator device. In this embodiment a wireless energy transfer from the wearable device to the neuro modulator device is enabled. The advantage of having a wearable electronic device is that the user or patient can easily and conveniently charge the neuro modulator device during normal daily life and/or during night sleep, especially in a pretty much any everyday situation, making it very convenient to operate the implanted neuro modulator device over a long period of time.

In a further preferred embodiment, the wearable electronic device comprises a wireless transmitting means, especially an antenna which is used for establishing a communication connection with the neuro modulator device and for transmitting energy to the neuro modulator device. According to this embodiment the electronic wearable device only comprises a single wireless transmitting means, especially antenna for both recharging the neuro modulator device and for transmitting data from the neuro modulator device to the wearable device and vice versa. This reduces the needed components for the wearable device.

In a further embodiment, the system comprises under pants, preferably made from fabric material, having retaining means, especially a fabric pocket, for retaining the neuro-modulator device. As previously, mentioned one possible application of the neuro modulator according to the current invention is modulating of nerves in the pubic area. After an implantation in this area of the body pants and especially underpants provide an advantage and convenient support structure to bring the wearable electronic device, especially any transmission means, such as an antenna, into a sufficient proximity with the implanted neuro modulator device when the underpants are worn by a patient or user. The electrical components can be integrated into parts of the fabric, for example is a fabric pocket or between layers of fabric, or into a housing made of different material as the underpants and fixed or connected to the underpants.

In an alternative but equally preferred embodiment, the wearable electronic device is detachably connected to a harness, preferably to a belt or a hip belt of the system. In other words, the system may comprise a belt, especially a hip belt, or a harness, having receiving means, especially self-securing means, for receiving and fixing the neuro-modulator device with the belt or harness. Similar to the previous embodiment of underpants, a belt or harness can be conveniently worn by a patient or user and can bring the wearable electronic device and its electronics, especially an antenna, into the necessary proximity with an implanted neuro modulator device in the pubic region in order to transmit energy and sent and/or receive date or information to and from the neuro modulator device.

According to a further preferred embodiment, the wearable electronic device is operable in at least two different operation modes, wherein the first mode is a charging and communication mode and wherein a second mode is a setup or programing or parameter selection mode. The second mode may be activated during the initial surgical implantation of the neuro modulator device. The second mode may also be activated after the wearable device is connected to a special device that is only available to medical professionals such as doctors and nurses. The second operation mode may enable the adaption of all sorts of programing and operation parameters of the neuro modulator device including critical operational parameters and settings.

In a further, preferred embodiment, the wearable electronic device is configured to perform a measurement indicative of the alignment, especially the special alignment with respect to the neuro modulator device, especially with respect to an antenna of the neuro modulator device. This can help the surgeon during the implantation surgery to position the neuro modulator device in such a fashion that the best possible alignment between the wearable device outside of the body and the implanted neuro modulator device inside the body is achieved, therefore allowing the best possible communication between the wearable device and the most effective energy transmission after the implantation.

In a further preferred embodiment, the wearable electronic device is configured to produce or cause an output, especially an audio output or visual output, indicating the relative position and/or orientation of the neuro modulator device, especially an antenna of the neuro modulated device with respect to the wearable electronic device, when operated in the setup or programing or parameter selection modes, that is the second operation mode. This is a convenient way to align the neuro modulator device to the wearable electronic device during initial implantation surgery.

BRIEF DESCRIPTION OF THE DRAWINGS

The invention is further described in more detail on the basis of the following drawings showing special embodiments of the invention. Those drawings show.

DETAILED DESCRIPTION

Figure 1:
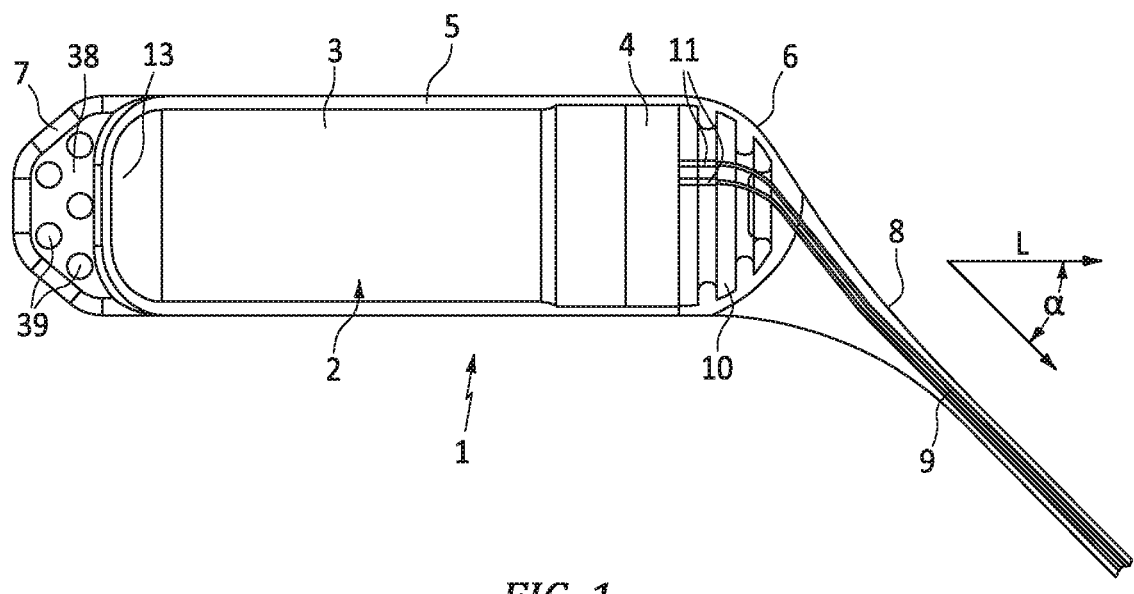
FIG. 1: A schematic view of an implantable neuro modulator device in a first embodiment of the invention.

FIG. 1 shows a first embodiment of an inventive implantable neuro modulator device 1. The neuro modulator device 1 has a housing 2 which comprises a first housing part 3 and a second housing part 4. Exterior to the first housing part 3 and the second housing part 4, an overmold 5 is molded onto the exterior surface of the housing 2.

In the embodiment of FIG. 1 the overmold 5 covers the entire housing 2 and further comprises a molded header 6 and a fixation wing 7. The fixation wing 7 and the molded header are arranged on opposite sides of the housing 2. The header 6 comprises a guide member 8 which is angled by 30° to 70° with respect to a longitudinal axis L of the neuro modulator device 1. The structured surfaces 38 of the fixation wing, which are connected to each other via the holes 39, and the electrode lead 9 guided within the guide member 8 are preferably arranged in parallel planes. The guide member 8 can be used to guide an electrode lead 9 to and away from the neuro modulator device 1, especially in a certain direction and/or orientation with respect to the housing and its interiors. The holes 39 may be used as suture holes or for autologous fixation of the device 1.

The fixation wing 7 and/or the electrode lead 9 within the guide member 8 may be arranged in parallel planes with respect to a receiving cross section of an antenna of the device (not shown in FIG. 1). Thus, the orientation of internal parts of the device can be known from the exterior design.

Inside the molded header 6 there is a fishbone member 10 that allows for a better adhesion and connection with the mold material in the region of the molded header 6. The electrode lead 9 is at least electrically connected to electrical contact elements 11 which extend through the second housing part 4 into the interior of the housing 2. The fixation wing 7, the overmold 5 and the molded header 6 can be made of a monolithic piece of molded material, preferably polymeric resin that is biocompatible.

The overmold 5, especially the molded header 6 are also adhered and/or fixed to the electrode lead 9, improving the un-detachable, permanent mechanical connection between the device and its antenna.

Figure 2:
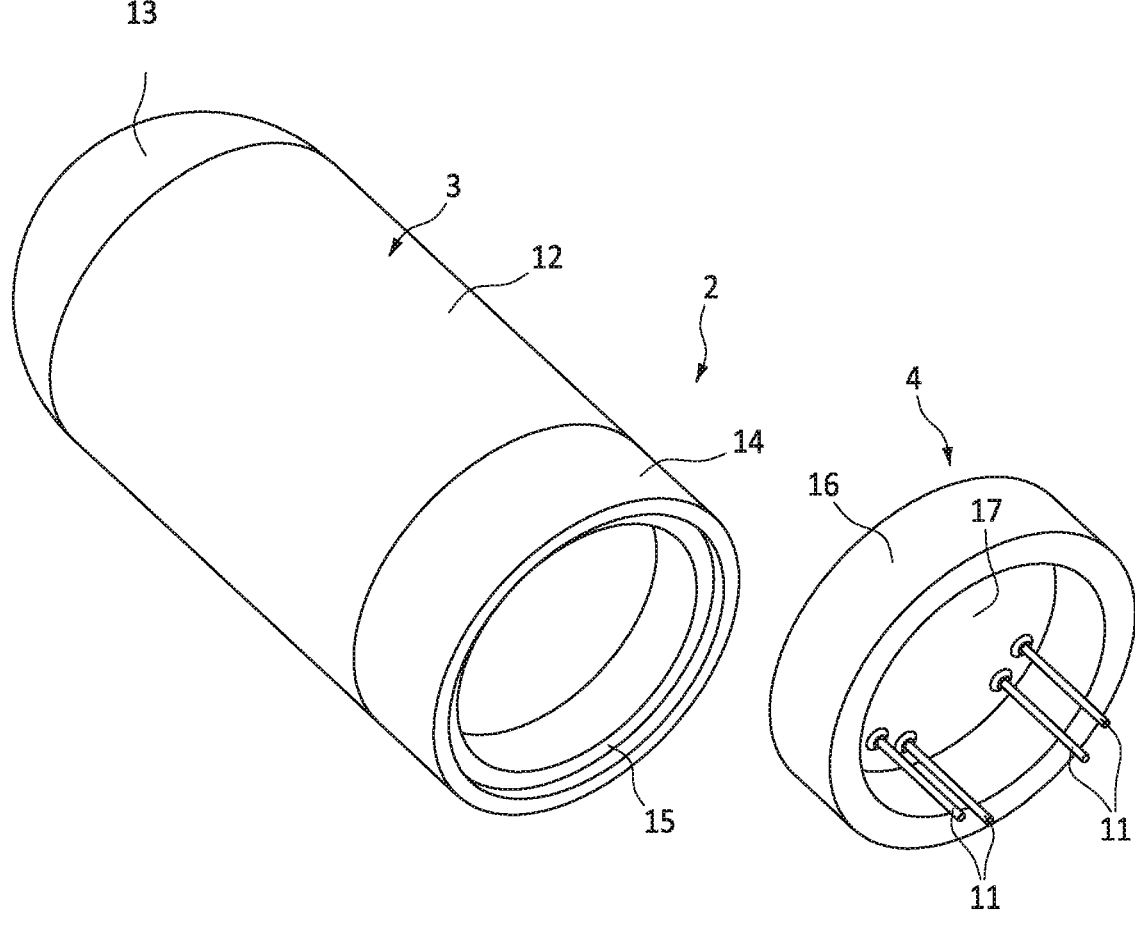
FIG. 2: A schematic view of a housing of an implantable neuro modulator device according to the invention.

FIG. 2 shows the housing 2 and the respective first housing part 3 and second housing part 4 in more detail. It can be seen that the first housing part 3 comprises a container 12 with a round cross section and a closed and rounded end 13 on one side and a first sealing ring 14 on the opposite side. The container 12 can preferably be made of a monolithic piece of ceramic material.

The first sealing ring 14 can preferably be made of titanium or surgical steel. As already can be seen from FIG. 2 an outward facing structure 14 of the first sealing ring 14 can have a stepped surface. The stepped surface may help to align and to seal the housing parts and/or the sealing rings 14, 16 with each other.

The second housing part 4 may also comprise a second sealing ring 16 and a feed-through element 17. The feed-through element 17 may have one or more openings 18 through which electrical contact elements 11 may electrically connect one side of the feed-through element 17 with the other side of the feed-through element 17. The feed-through element 17 may also be made of ceramic material and may have a disk shape or disk form. The feed-through element 17 may be placed entirely within the inner space of the second sealing ring 16.

The openings 18 can be arranged on two different height levels as shown in FIG. 2 wherein a height levels are defined by lines perpendicular to a diameter line through the center of the feed-through element 17.

FIG. 2 shows the first housing part 3 and the second housing part 4 detached from one another in an open state of the housing 2. By sealing the first sealing ring 14 and second sealing ring 16 together, preferably by a gold brazing, the housing 2 can be hermetically sealed, especially when the space in between the electrical contact elements 11 and the openings 18 are also filled with a gold brazing or an alternative material securing the electrical isolation of the contact elements 11.

Figure 3:
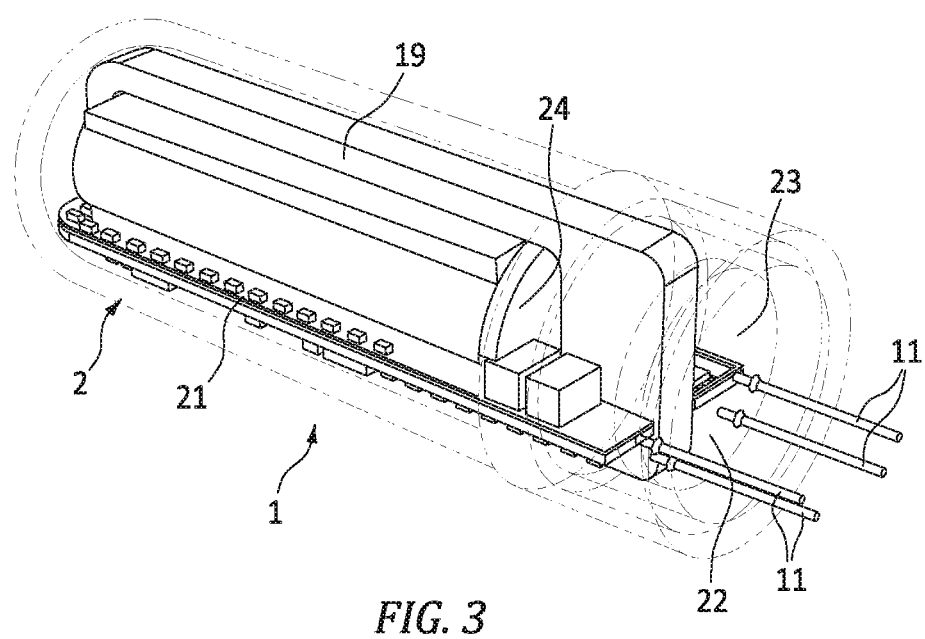
FIG. 3: A schematic view of an implantable neuro modulator device according to the invention.

FIG. 3 depicts an implantable neuro modulator device 1 similar to the embodiment of FIGS. 1 and 2 in which the housing 2 is displayed in a semi-transparent mode. The overmold is not shown in FIG. 3. In this depiction, the two sealing rings 14 and 16 cannot clearly be distinguished. However, the interior of the neuro modulator device 1 can be seen. Inside the housing 2 of the neuro modulator device 1 there is an antenna 19, a rechargeable energy storage device 20 and a support member 21. The support member 21 supports the other components, especially the electronic or electric components of the neuro modulator device 1, mechanically and connects them electrically. The support member 21 also provides for the connection to the electrical contact element 11, although this connection is not clearly visible in the presentation of FIG. 3. The support member 21 can comprise a printed circuit board (PCB).

The embodiment of FIG. 3 shows a single rechargeable energy storage device 20. In an alternative and advantageous embodiment two or more rechargeable energy storage devices 20 could be used.

The support member 21 is arranged eccentrically within the interior of the housing 2 and divides the internal space of the housing into a first cavity 22 with a smaller volume and a second cavity 23 with a larger volume. The rechargeable energy storage device 20 is arranged within the second cavity 23 and is also further arranged within the aperture or receiving cross section 24 of the antenna 19.

If two or more rechargeable energy storage device 20 are used, they could all advantageously be arranged within the second larger cavity 23 and also further arranged within the aperture or receiving cross section 24 of the antenna 19.

The antenna 19 may be made of several layers of printed circuit board, each carrying one or more printed windings of an antenna coil. The antenna 19 may also be electrically connected to the support member 21. In an alternative preferred embodiment, the antenna could also comprise several windings of an, preferably uninterrupted, wire which is wound onto a carrier structure, preferably from a material that is electromagnetically transparent, similar to the materials usable for the housing defined above. Preferably the carrier structure could be made from 3D-pintined or from injection molded plastic. The carrier structure could be made of one or more pieces.

The antenna 19 has an essentially rectangular shape. The antenna 19, especially the receiving cross section 24 of the antenna 19, is preferably arranged at an angle, especially at a right angle to the plane of the support member 21. The way in which the antenna 19 is mounted over or around the support member 21 and the rechargeable energy storage device 20 will become more apparent with respect to the FIGS. 5 to 6. The antenna 19 is designed as a large aperture antenna, preferably with a receiving cross section 24 of more than 0.1*A*B, A being the length of the housing 2 and B being the width or diameter of the housing 2.

Figure 4:
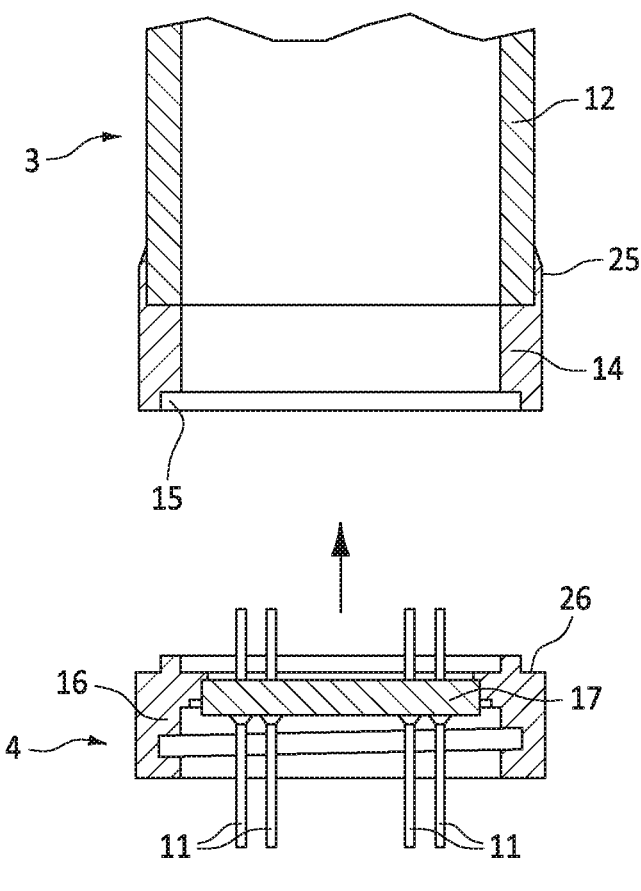
FIG. 4: A schematic view of a housing of an implantable neuro modulator device according to the invention.

FIG. 4 show parts of the first housing part 3 and the second housing part 4, including the first sealing ring 14 and the second sealing ring 16. It is visible that additionally to the stepped outward facing structure 15 the first sealing ring 14 has a sleeve extension 25 on an opposite end to receive the container 12 in the said sleeve extension 25. This facilitates the arrangement and connection of the container 12 and the first sealing ring 14.

The stepped outward facing structure 15 is used to get into contact with a respectively stepped inward facing surface 26 of the second sealing ring 16, facilitating the alignment and the connection or sealing of the first sealing ring 14 and the second sealing ring 16.

Figure 5A:
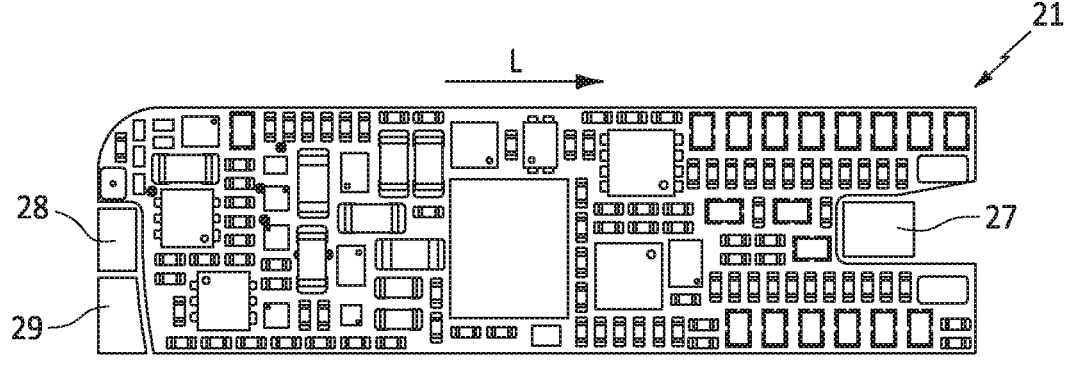
FIG. 5*a*: A schematic view of a first side of a support member of an implantable neuro modulator device according to the invention.

FIG. 5*a* shows a first side of the support member 21 carrying electronic components, such as microcontrollers, OP-Amps, FETs, passive components and the like. The support member 21 has a first passageway 27 and a second passageway 28 on opposite sides in a length or longitudinal direction L of the support member 21. Perpendicular to the image plane of FIG. 5*a* the antenna 19 can pass through the support member in said passage ways 27 and 28. To be able to slide the antenna over the support member 21 and/or the rechargeable energy storage device 20, the support member 21 further comprises a cutout 29 that enables the support member to be arranged at an angle, preferably at a right angle with respect to the antenna 19 and further enables the antenna 19 to pass the support member or to stretch onto both sides of the support member 21.

The cutout 29 could be eliminated, when a wire coil antenna which is wound onto a carrier structure would be used instead of an antenna based on a plurality of PCB layers. In this case the carrier structure may be made of two different parts which can be fixed to both sides of the support member 21. The coil could then be wound onto the carrier after said carrier structure is placed on top and below the support member 21. In this embodiment (not shown in the Figures) the passageways could also be made smaller or eliminated.

Figure 5B:
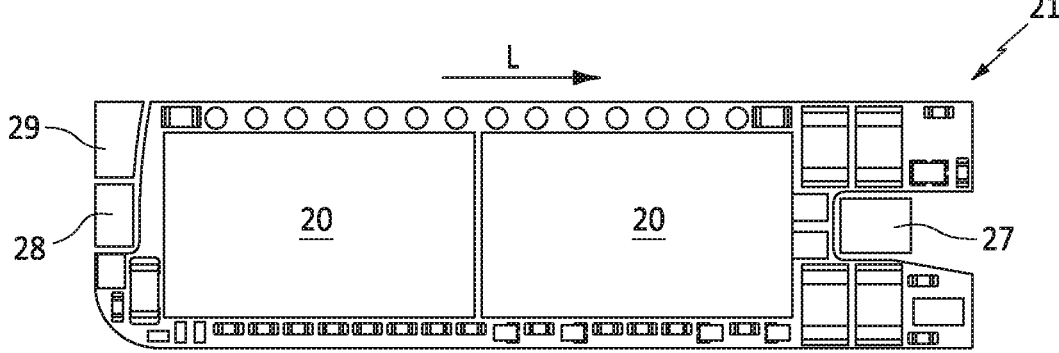
FIG. 5*b*: A schematic view of a second side of a support member of an implantable neuro modulator device according to the invention.

FIG. 5*b* shows the opposite side of the support member 21, again with the passageways 27 and 28 and the cutout 29. In the depiction of FIG. 5*b* there are two rechargeable energy storage devices 20 arranged on the second side of the support member 21. The two rechargeable energy storage devices 20 can preferably be solid state batteries.

Figure 6A:
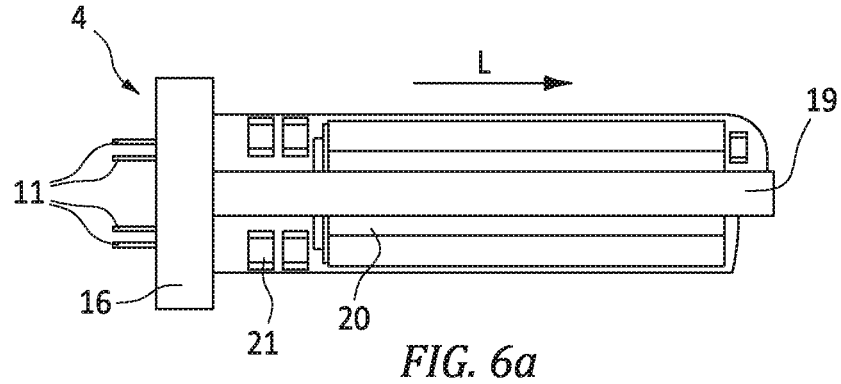
FIG. 6*a*: A schematic view of pre-assembled parts of an implantable neuro modulator device according to the invention.

FIG. 6*a* shows a preassembled part of the implantable neuro modulator device 1 in which the second housing part 4 including the electrical contact elements 11 are electrically connected to the support member 21 which is in turn connected to the rechargeable energy storage device 20 and the antenna 19. FIG. 6*a* shows the preassembled part in a view parallel to the plane of the support member 21. The plane of the receiving cross section 24 or aperture of the antenna 19 is arranged at right angles to the plane of the support member.

Figure 6B:
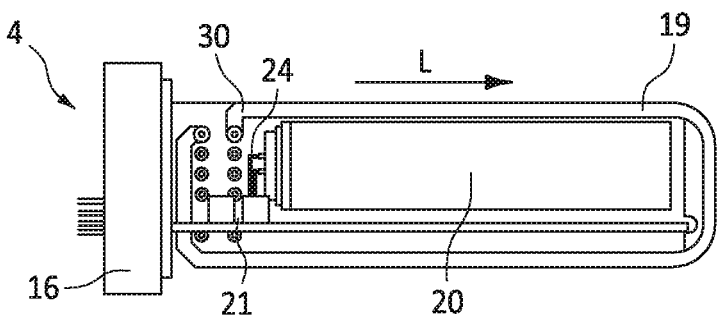
FIG. 6*b*: A schematic view of pre-assembled parts of an implantable neuro modulator device according to the invention.

FIG. 6*b* shows a view onto the preassembled part of the implantable neuro modulator device 1 according to FIG. 6*a* turned by approximately 90° about the longitudinal axis L. In this view, the receiving cross section 24 of the antenna 19 is parallel to the picture plane and the support member 21 or the plane of the support member 21 is at a right angle with respect to the receiving cross section 24 and the image plane. In this representation the single antenna windings 30 formed on the multitude of printed circuit board layers being arranged adjacent to one another forming the antenna 19 are partly visible.

It is also visible from FIG. 6*b* that the support member 21 is arranged eccentrically with respect to the cross section or a diameter of the housing 2.

Figure 7A:
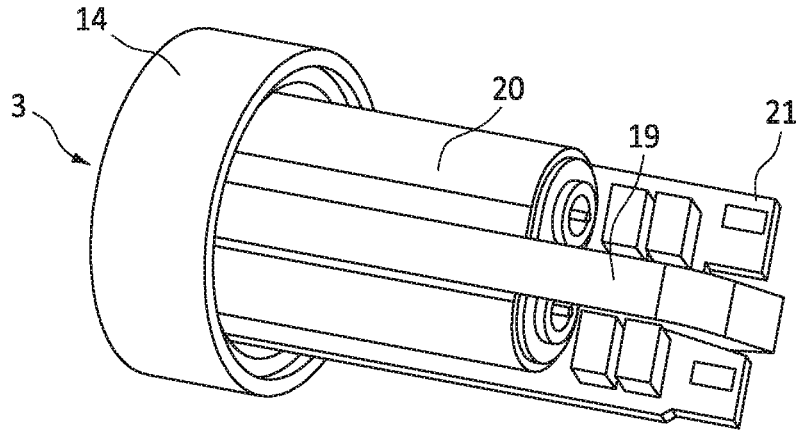
FIG. 7*a-c*: A schematic view of pre-assembled parts of an implantable neuro modulator device according to the invention.
Figure 7B:
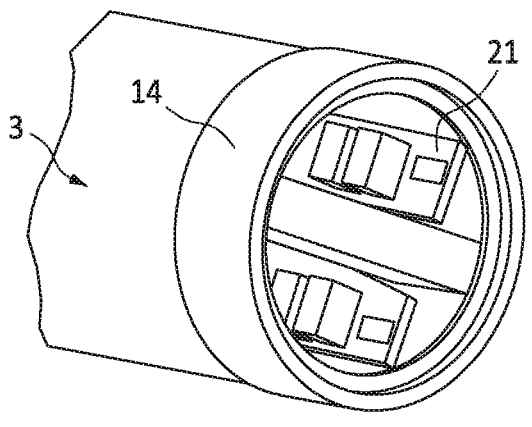
Figure 7C:
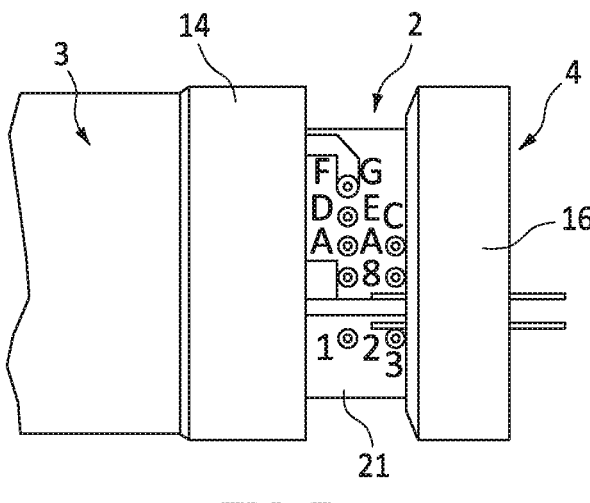

FIGS. 7*a* to 7*c* show other representations of the support member 21 with multiple electrical and electronic components attached to it. Together with the antenna 19 and the rechargeable energy storage device 20 the support member

21 is placed within the first housing part 3 through the opening of the first sealing ring 14.

FIG. 7*b* depicts the support member 21 as well as the antenna 19 in a state in which they are fully inserted into the housing, especially the first housing part 3. The support member 21 extends essentially over the entire length of the interior of the first housing part 3 and over the entire width of the interior of the first housing part 3 at the eccentric height level. Since the second housing part 4, as depicted in FIGS. 2, 4 and 7*c* does not significantly add to the length or width of the interior space of the housing 2 this also means that the support member 21 and the antenna 19 are preferably extending over essentially the entire length and the entire width of the internal space of the housing 2.

Figure 8:
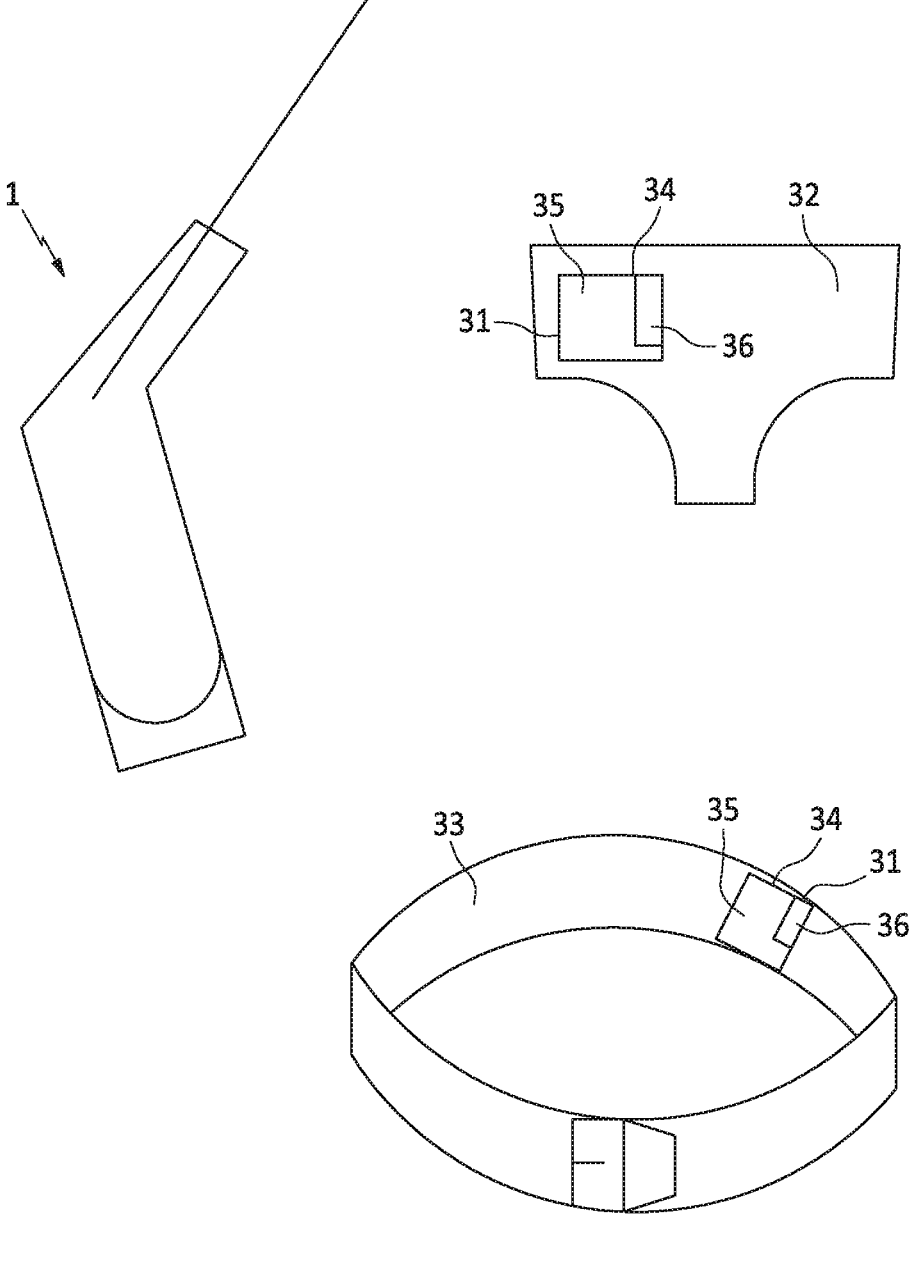
FIG. 8: A schematic view of an inventive system including an implantable neuro modulator device according to the invention and a wearable electronic device.

FIG. 8 shows a possible embodiment of an inventive system comprising an inventive implantable neuro modulator device 1. The system further comprises two wearable and/or handheld electronic devices 31. The system only requires one wearable and/or handheld electronic device 31 (hereinafter: wearable device). The two wearable devices 31 only show different embodiments of wearable devices 31 that may operate within the inventive system.

One of those wearable devices 31 can be inserted into a pair of underpants 32 of the system, preferably made of fabric material. The second wearable device 31 comprises a harness, especially a belt 33, preferably a hip belt. Both wearable devices 31 comprise wireless transmitting means 34 which are connecting to a wireless energy transmitting unit 35 and combined input and output interface 36, such as a touch display, of the wearable electronic device 31. The combined input and output interface 36 may also be replaced by single input interfaces such as buttons and one or more output interfaces such as a display.

The wireless transmitting means 34 can be connected to the neuro modulator device 1 via the antenna 19 not shown in FIG. 8. The combined input and output interface 36 may be used to control the wearable device 31 and thereby also remote-controlling the neuro modulator device 1. The wearable device 31 may operate in a first operation mode, accessible to all users and a second operation mode only accessible to medical professionals.

When neuro modulator device 1 is brought into proximity to the wearable device 31, especially wireless transmitting means 34 of the wearable device 31, the wearable device 31 can be used to charge the neuro modulator device 1 and to send and/or receive data or information to and from the neuro modulator device 1.

The patient or user may change a first set of parameters of the neuro modulator device 1 by an input to the combined input and output interface 36 of the wearable device 31. In the first operation mode a first set of parameters can be defined such that changing the parameters has an effect on patient conform or convenience. In the second operation mode the second set of parameters which can be changed may include the first set of parameters as well as further parameters and may preferably include parameters that relate to the more general and critical operation features of the neuro modulator device 1.

LIST OF REFERENCE SIGNS

1 Implantable neuro modulator device
2 Housing
3 First housing part
4 Second housing part
5 Overmold
6 Molded header 7 Fixation wing
8 Guide member
9 Electrode lead
10 Fishbone member
11 Electrical contact element
12 Container
13 End
14 First sealing ring
15 Outward facing structure
16 Second sealing ring
17 Feed-through element
19 Antenna
20 Rechargeable energy storage device
21 Support member
22 First cavity
23 Second cavity
24 Receiving cross section
25 Sleeve extension
26 Inward facing surface
27 First passageway
28 Second passageway
29 Cutout
30 Windings
31 Wearable device
32 Underpants
33 Belt
34 Wireless transmitting means
35 Wireless energy transmitting unit
36 Communication interface
38 Surface
39 Holes
L Longitudinal axis

The invention claimed is:

1. Implantable neuro-modulator device, comprising a hermetically sealed housing (2),
    wherein an antenna (19) for communicating with external devices and/or for wirelessly receiving electrical energy is positioned within the housing (2), wherein a major part of the housing (2) is electromagnetically transparent to radiation in the frequency range below 20 MHz, wherein the housing (2) has a round cross section, and comprises a first housing part (3) and a second housing part (4), wherein the first housing part (3) comprises a container (12) with a round cross section which is closed at one end (13) and has a first sealing ring (14) at the opposite or second end.

2. Neuro-modulator device according to claim 1,
    wherein the electromagnetically transparent part of the housing is made from plastics, resin, glass, ceramics or a combination thereof.

3. Neuro-modulator device according to claim 1,
    wherein the container (12), together with the closed end (13), are machined from a monolithic piece of material.

4. Neuro-modulator device according to claim 1,
    wherein the second housing part (4) comprises a second sealing ring (16) and a feed-through element (17), the feed through element (17) comprising at least one opening (18) in which an electrical contact element (11) may electrically connect one side of the feed-through element (17) with a second side of the feed-through element (17).

5. Neuro-modulator device according to claim 4,
    wherein the contact element (11) is electrically connected to an electrode lead (9) for outputting modulation pulses to a patient.

6. Neuro-modulator device according to claim 1, comprising an overmold (5) including a molded header (6) made of biocompatible polymeric resin, the molded header (6) covering at least parts of the electrical contact element (11) and the respective openings (18) in the feed-through element (17) on one side of the feed-through element (17).

7. Neuro-modulator device according to claim 6,
    wherein the overmold (5) comprises at least one opening and/or suture hole for autologous fixation of the device and/or for suturing the device to tissue or bone material.

8. Neuro-modulator device according to claim 6,
    wherein an end portion of the molded header (6), opposite to the second housing part (4), comprises a guide member (8) for guiding an electrode lead (9), wherein the guide member (8) is formed at an angle with respect to a longitudinal axis (L) of the housing (2).

9. Neuro-modulator device according to claim 6,
    wherein the overmold (5) is covering the entire first and second housing part (3,4) and further forming a molded header (6) and/or a fixation wing (7).

10. Neuro-modulator device according to claim 9,
    wherein the fixation wing (7) is formed at an end of the housing (2), either adjacent to the first housing part (3) or opposite to the molded header (6) and the electrode lead (9).

11. Neuro-modulator device according to claim 9,
    wherein the fixation wing (7) is formed in a plane parallel to a longitudinal axis (L) of the housing (2) in the same or parallel plane as the electrode lead (9) within the guide member (8).

12. Neuro-modulator device according to claim 1,
    wherein a diameter-to-length ratio of the housing's maximum diameter to the length of the housing (2) is less than 0.35.

13. Neuro-modulator device according to claim 1,
    wherein the housing (2) has a maximum diameter of less than 12 mm.

14. Neuro-modulator device according to claim 1,
    wherein additionally at least one antenna (19), one rechargeable energy storage device (20) and one electrical control unit and a pulse generating means are arranged within the housing (2).

15. Neuro-modulator device according to claim 1,
    wherein a support member (21) extends essentially over an entire length and an entire width of an internal space confined by the housing (2) at a certain eccentric height-level of the housing (2), dividing the space confined by the housing into a first, smaller and second, larger cavity (22, 23) of the housing (2), each one defined by parts of the housing (2) and one side of the support member (21), respectively.

16. Neuro-modulator device according to claim 14,
    wherein the at least one rechargeable energy storage device (20) is/are placed in a second, larger cavity (23) of the housing (2).

17. Neuro-modulator device according to claim 1,
    wherein the at least one antenna (19) is designed as a large aperture antenna with a receiving cross section of more than 0.1*A*B, A being the length of the housing and B being the width or diameter of the housing.

18. Implantable neuro-modulator device, comprising a hermetically sealed housing (2),
    wherein an antenna (19) for communicating with external devices and/or for wirelessly receiving electrical energy is positioned within the housing (2), wherein a major part of the housing (2) is electromagnetically transparent to radiation in the frequency range below 20 MHz,
    wherein the length of the housing (2) is less than 50 mm.

19. Neuro-modulator device according to claim 18, wherein the housing (2) has a round cross section, and comprises a first housing part (3) and a second housing part (4), wherein the first housing part (3) comprises a container (12) with a round cross section which is closed at one end (13) and has a first sealing ring (14) at the opposite or second end.

20. Neuro-modulator system comprising an implantable neuro-modulator device (1) comprising a hermetically sealed housing (2),
wherein an antenna (19) for communicating with external devices and/or for wirelessly receiving electrical energy is positioned within the housing (2), wherein a major part of the housing (2) is electromagnetically transparent to radiation in the frequency range below 20 MHz,
and a wearable and/or handheld electronic device (31),
wherein the wearable and/or handheld electronic device (31) comprises an energy storage device and a communication interface for establishing a communication connection with the neuro-modulator device (1).

\* \* \* \* \*